United States Patent [19]
Hardtmann

[11] 3,931,178
[45] *Jan. 6, 1976

[54] 1-SUBSTITUTED-2-IMINO-PYRIDO[2,3-D]PYRIMIDIN-4(1H)-ONES
[75] Inventor: Goetz E. Hardtmann, Florham Park, N.J.
[73] Assignee: Sandoz Inc., E. Hanover, N.J.
[ * ] Notice: The portion of the term of this patent subsequent to Jan. 6, 1993, has been disclaimed.
[22] Filed: July 24, 1974
[21] Appl. No.: 491,250

Related U.S. Application Data
[63] Continuation-in-part of Ser. No. 437,470, Jan. 28, 1972, abandoned, which is a continuation-in-part of Ser. No. 373,475, June 25, 1973, abandoned.

[52] U.S. Cl... 260/256.4 F; 260/247.7 K; 260/294.8 R; 424/250
[51] Int. Cl.² ................................ C07D 239/00
[58] Field of Search ............................ 260/256.4 F

[56] References Cited
UNITED STATES PATENTS
3,794,637   2/1974   Wiedemann et al. ........ 260/256.4 F Primary Examiner—Donald G. Daus
Assistant Examiner—James H. Turnipseed
Attorney, Agent, or Firm—Gerald D. Sharkin; Richard E. Vila

[57] ABSTRACT

ANTI-HISTAMINICS OF THE FORMULA:

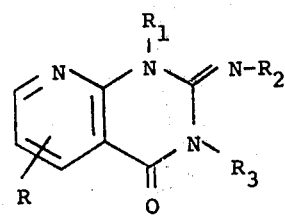

wherein
  $R_1$ is alkyl, alkenyl or phenalkyl,
  $R_2$ and $R_3$ are hydrogen, alkyl or alkenyl, and
  R is an optional substituent, are prepared by reacting a 3,4-dihydro-1,3-dioxo-1H-pyrido [2,3-d][1,3]oxazine (a 3-azaisatoic anhydride) with a S-methyl-thiopseudourea.

15 Claims, No Drawings

1-SUBSTITUTED-2-IMINO-PYRIDO[2,3-D]PYRIMIDIN-4(1H)-ONES

This application is a continuation-in-part of application Ser. No. 437,470, filed Jan. 28, 1974, which in turn is a continuation-in-part of copending application Ser. No. 373,475, filed June 25, 1973, now all abandoned.

This invention relates to 1,2-disubstituted-pyrido[2,3-d]pyrimidin-4(1H)-ones, their preparation and intermediates useful in their preparation and to compositions and methods utilizing the pharmacological activity of said compounds.

The compounds of the invention may be represented by the structural formula I:

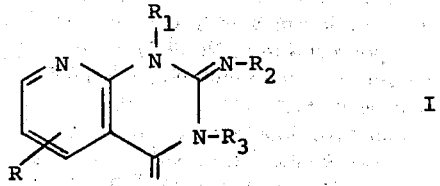

wherein
$R_1$ is alkyl of 1 to 6 carbon atoms, alkenyl of 3 to 8 carbon atoms or phenalkyl of the formula II:

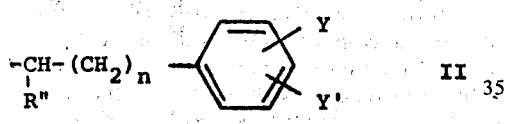

$n$ is 0 to 1,

R'' is hydrogen or methyl, preferably with R'' being hydrogen when n is 1, $R_2$ is hydrogen, alkyl of 1 to 6 carbon atoms or alkenyl of 3 to 6 carbon atoms, $R_3$ is hydrogen, alkyl of 1 to 6 carbon atoms or alkenyl of 3 to 6 carbon atoms.

R is hydrogen or alkyl of 1 to 3 carbon atoms, and

Y and Y' are independently hydrogen, halo of atomic weight of from 18 to 36, alkyl of 1 to 3 carbon atoms or alkoxy of 1 to 3 carbon atoms or one is hydrogen and the other bromo or trifluoromethyl.

The compounds of the formula (I) having the formula (Ia):

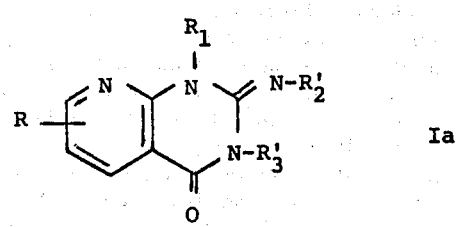

in which R and $R_1$ are as defined, and $R_2'$ and $R_3'$ are the same respectively as $R_2$ and $R_3$ as above defined but subject to the proviso that $R_2'$ is a hydrocarbon when $R_3'$ is a hydrocarbon may be prepared in a Step A reaction involving reacting a compound of the formula (III):

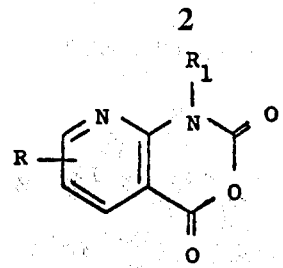

wherein R and $R_1$ are as defined, with a compound of the formula (IV):

wherein $R_2'$ and $R_3'$ are as defined.

The compounds of the formula I having the formula Ib:

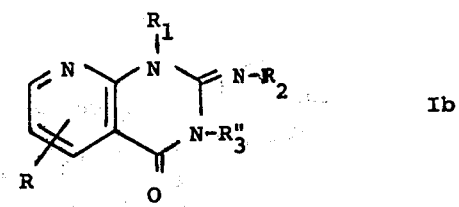

in which R, $R_1$ and $R_2$ are as above defined and $R_3''$ is alkyl of 1 to 6 carbon atoms or alkenyl of 3 to 6 carbon atoms may also be prepared in a Step B reaction by reacting a compound of the formula Ic:

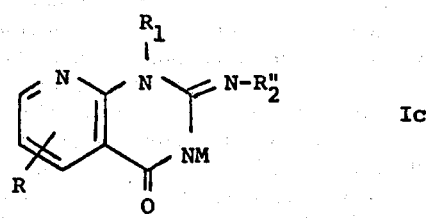

in which R and $R_1$ are as defined, M is hydrogen or an alkali metal, preferably sodium and $R_2''$ is hydrogen, alkyl of 1 to 6 carbon atoms, alkenyl of 3 to 6 carbon atoms or M as above defined, with an alkylating agent of the formula V:

$$X-R_3''  \qquad V$$

in which $R_3''$ is as above defined and X is halo of atomic weight of from 35 to 127, preferably iodo.

The compounds of the formula I having the formula Id:

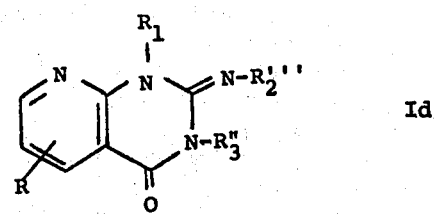

in which R, $R_1$ and $R_3''$ are as defined and $R_2'''$ is alkyl of 1 to 6 carbon atoms or alkenyl of 3 to 6 carbon atoms may also be prepared in a Step C reaction by reacting a compound of the formula Ie:

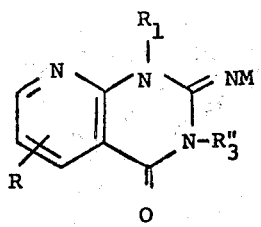

in which M, R, $R_1$ and $R_3''$ are as defined, with an alkylating agent of the formula VI:

$$X-R_2''' \qquad \text{VI}$$

in which X and $R_2'''$ are as defined.

The compounds of the formula Ia, defined above, may also be prepared in a Step D reaction involving cyclizing a compound of the formula VII:

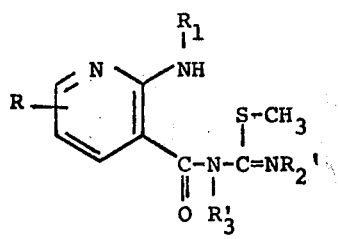

wherein R, $R_1$, $R_2'$ and $R_3'$ are as defined.

The preparation of compounds Ia by the reaction of Step A can be carried out at elevated temperatures, typically in the range of at least 80°C. to 200°C., preferably 120°C. to 180°C. The reaction is conveniently carried out in an organic solvent of conventional type providing an inert reaction medium. The higher boiling solvents for use at reflux temperatures represent the preferred solvents, e.g., xylene and especially diglyme and the like. The reaction is preferably carried out in the presence of a base, e.g. potassium carbonate; and when the compound IV is employed directly in acid addition salt form, it is of course desirable to employ an amount of base greater than the amount necessary to neutralize the acid. It will be appreciated by those skilled in the art that the compounds of the formula IV are tautomeric and have the alternative and equivalent structure represented by the formula IVA:

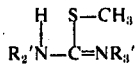

wherein $R_2'$ and $R_3'$ are as above defined. It thus may be foreseen that the reaction of Step A in which $R_2'$ and $R_3'$ in the compounds IV (and IVA) are dissimilar alkyls and/or alkenyls may lead to mixtures of the final products of the formula Ia. Accordingly, the final products in $R_2'$ and $R_3'$ are dissimilar hydrocarbon groups may in some instances be preferably prepared by the reaction of Step B and Step C. In general, the reaction product of formula Ia may be recovered from the reaction of Step A by working up by conventional procedures.

The reaction of Step B is of known type and preferably effected employing a compound Ic in which M is an alkali metal. Such compounds Ic may be prepared from the corresponding compound Ic in which M is hydrogen in a known manner involving the reaction of a compound Ic in which M is hydrogen with a strong base such as an alkali metal hydride or alkoxide, preferably sodium hydride. The reaction is conveniently effected at from 0°C. to 50°C., preferably at about room temperature, in an inert solvent which can be employed as solvent for the reaction of Step B. The conversion of the metallo substituted pyrimidinone of the formula Ic to the desired product may be carried out at temperatures of from 0°C. to 100°C., preferably 10°C. to 40°C. and conveniently at room temperature. When the Step B reaction is carried out with a compound Ic in which M is hydrogen, the reaction is conducted in the presence of a strong base, e.g., sodium hydride. In either case, the conditions of time, temperature and quantity of strong base and compound V are generally controlled based on the premise that the alkylation or alkenylation of Step B will favor the 3- position of the compound of the formula Ic. For example, when employing a compound of the formula Ic in which $R_2''$ is hydrogen, the more controlled or limited conditions would favor the production of the compound of the formula Ib in which $R_2$ is hydrogen. On the other hand, increased quantities of the strong base and alkylating or alkenylating agent and the longer reaction times and higher temperatures will result in increased quantities of the compound of the formula Ib in which $R_2$ and and $R_3''$ are similar alkyl or alkenyl groups. Since the compounds of the formula I in which $R_2$ and $R_3$ are similar are very conveniently prepared by the Step A reaction, it will be evident that the reaction of Step B should merit serious consideration only when producing final products in which $R_3$ is a hydrocarbon group and $R_2$ and $R_3$ are dissimilar.

The reaction of Step C and the preparation of the intermediate of the formula Ie in which M is an alkali from a compound Ie in which M is hydrogen is carried out analogously to the reaction of Step B. It will be evident from the foregoing that Step C should also only merit serious consideration when producing compounds of the formula Id in which $R_2'''$ and $R_3''$ are dissimilar hydrocarbon groups.

The preparation of compounds of the formula Ia by the reaction of Step D may be carried out by heating a compound of the formula VII at elevated temperatures preferably in the range of 120°C. to 200°C., more preferably 130°C. to 180°C. and desirably in the presence of an inert solvent and strong base. The inert solvents may be of conventional type and are preferably the higher boiling solvents, e.g., diglyme. Suitable strong bases include the strong inorganic bases such as the alkali metal hydroxides, e.g. sodium hydroxide. Reaction time may vary, particularly with temperature, with good results usually obtained in one-half to ten hours.

The compounds of the formula VII employed in Step D may be prepared by reacting a compound of the formula III with a compound of the formula IV under controlled temperature and time conditions. In general, temperatures are usually in the range of from 20°C. to 120°C., preferably 60°C. to 115°C. Reaction times may be typically of the order of from 10 minutes to 5 hours and generally will vary inversely with reaction temperature. The reaction is preferably carried out in the presence of a base such as an inorganic base, e.g., potassium carbonate, and in the presence of an inert solvent of conventional tupe. The solvents boiling at reflux temperatures are generally preferred, e.g., benzene and toluene. The resulting product of the formula VII may, if desired, be isolated and recovered by working up by conventional procedures.

It will be evident that the compounds of the formula VII in which $R_3'$ is hydrogen exist in and be expressed by the alternative and equivalent tautomeric form having the formula VIIA:

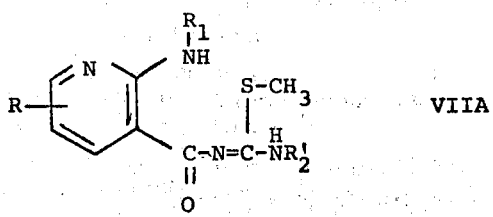

in which R, $R_1$ and $R_2'$ are as defined.

The compounds of the formulae III, IV, V and VI are either known or may be produced from known materials by established procedures.

The compound of the formula I in which both $R_2$ and $R_3$ are hydrogen form acid addition salts and the pharmaceutically acceptable acid addition salts not materially depreciating the pharmacological effect of said compounds are included within the scope of the compounds of the formula I of the invention. Such salts include the well known pharmaceutically acceptable salts, e.g., the hydrochloride, maleate, etc. The acid addition salts may be produced from the corresponding free base by conventional procedures. Conversely, the free bases may be obtained from the salts by procedures known in the art.

The compounds of formula I of the invention are useful because they possess biological activity. In particular, the compounds of the formula I are useful as agents for relieving the symptomatic effects of the release of histamine, i.e., as anti-histaminic agents, as indicated by observing the respiratory status on oral administration (5–100 mgs./kgs.) to the unanesthetized guinea pig exposed to aerosolized histamine dihydrochloride according to a modification of the method of Van Arman et al., J. Pharmacol, Exptl. Therap. 133: 90–97, 1961. For such use and depending upon known variables satisfactory results are obtained in general on the daily administration of from 1 to 100 milligrams per kilogram of body weight, preferably given in divided doses to 2 to 4 times a day, or in sustained release form. For most mammals the administration of from 60 to 2000 milligrams per day provides satisfactory results and dosage forms suitable for internal administration comprise 15 to 1000 milligrams of the compound in admixture with a solid or liquid pharmaceutical carrier or diluent.

The preferred compounds of the invention from the standpoint of anti-histaminic activity are those in which $R_1$ is benzyl including substituted benzyl, particularly unsubstituted benzyl or halobenzyl, e.g. fluorobenzyl, especially 4-halobenzyl, and the more preferred compounds are those in which R is hydrogen and/or $R_2$ is alkyl, more preferably of 1 to 3 carbon atoms and more preferably with $R_3$ being hydrogen.

For the use indicated above, the compounds may be combined with a pharmaceutically acceptable carrier, and such other conventional adjuvants as may be necessary, and administered orally or parenterally. For most uses oral administration with carriers is preferred and may take place in such conventional forms as tablets, dispersible powders, granules, capsules, suspensions, syrups and elixirs. Such compositions may be prepared according to any method known in the art for the manufacture of pharmaceutical compositions, and such compositions may contain one or more conventional adjuvants, such as sweetening agents, flavoring agents, coloring agents and preserving agents, in order to provide an elegant and palatable preparation. Tablets may contain the active ingredient in admixture with conventional pharmaceutical excipients, e.g., inert diluents such as calcium carbonate, sodium carbonate, lactose and talc, granulating and disintegrating agents, e.g., starch and alginic acid, binding agents, e.g., starch, gelatin and acacia, and lubricating agents, e.g., magnesium stearate, stearic acid and talc. The tablets may be uncoated or coated by known techniques to delay disintegration and adsorption in the gastro-intestinal tract and thereby provide a sustained action over a longer period. Similarly, suspensions, syrups and elixirs may contain the active ingredient in admixture with any of the conventional excipients utilized for the preparation of such compositions, e.g., suspending agents (methylcellulose, tragacanth and sodium alginate), wetting agents (lecithin, polyoxyethylene stearate and polyoxyethylene sorbitan monooleate) and preservatives (ethyl-p-hydroxybenzoate). Capsules may contain the active ingredient alone or admixed with an inert solid diluent, e.g., calcium carbonate, calcium phosphate and kaolin. The preferred pharmaceutical compositions from the standpoint of preparation and ease of oral administration are solid compositions, particularly hard-filled capsules and tablets. Parenteral administration may be in such conventional forms as injectionable solutions and suspensions.

A representative formulation is a tablet for oral administration 2 to 4 times a day for relieving the effects of histamine release and prepared by conventional tabletting techniques to contain the following ingredients:

| Ingredients | Weight (mg.) |
|---|---|
| 1-(4'-fluorobenzyl)-2-methylamino-pyrido[2,3-d] pyrimidin-4(1H)-one | 25 |
| Tragacanth | 10 |
| Lactose | 222.5 |
| Corn Starch | 25 |
| Talcum | 15 |
| Magnesium Stearate | 2.5 |

It will be evident to those skilled in the art that the compounds of the formula I in which $R_3$ is hydrogen are tautomeric and have the alternative and equivalent structure represented by the formula IA:

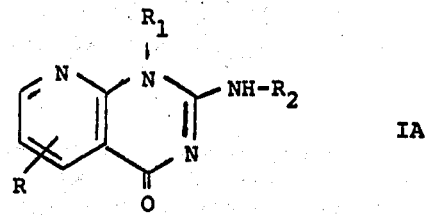

wherein R, $R_1$ and $R_2$ are as defined.

The following examples show representative compounds encompassed within the scope of this invention and the manner in which such compounds are prepared. However, it is to be understood that the examples are for purposes of illustration only.

EXAMPLE 1

1-(4'-fluorobenzyl)-2-methylamino-pyrido[2,3-d]pyrimidin-4(1H)-one.

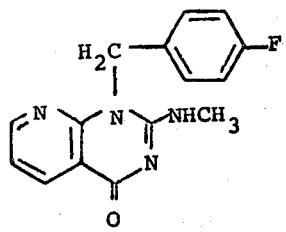

A mixture of 25 g. of 4-(4'-fluorobenzyl)-3,4-dihydro-1,3-dioxo-1H-pyrido[2,3-d][1,3]oxazine, 15 g. of S,N-dimethyl-thiopseudourea (hydrogen iodide), 15 g. of anhydrous potassium carbonate and 300 ml. of diglyme is refluxed with stirring for 4 hours. The resulting mixture is filtered while hot through Celite and the precipitate formed on cooling is recovered by filtering, washed with diglyme and then three times with ether and then dried under reduced pressure. The resulting product is dissolved in methylene chloride/methanol, filtered to remove insoluble material, concentrated on a steam bath and treated with ether to crystallize the titled produce (free base form), m.p. 242–246°C.

EXAMPLE 2

Following the procedure of Example 1 the following compounds of the invention are prepared:
a. 1-ethyl-2-methylamino-pyrido[2,3-d]pyrimidin-4(1H)-one, m.p. 275°–280°C.
b. 1-(4'-fluorobenzyl)-2-methylamino-3-methyl-2,3-dihydro-pyrido[2,3-d]pyrimidin-4(1H)-one, m.p. 112°–114°C.
c. 1-(4'-fluorobenzyl)-2-ethylamino-pyrido[2,3-d]pyrimidin-4(1H)-one, m.p. 249°–253°C.
d. 1-(4'-fluorobenzyl)-2-methylamino-7-methyl-pyrido [2,3-d]pyrimidin-4(1H)-one.

EXAMPLE 3

1-(4'-fluorobenzyl)-2,3-dihydro-2-imino-3-methyl-pyrido [2,3-d]pyrimidin-4(1H)-one.

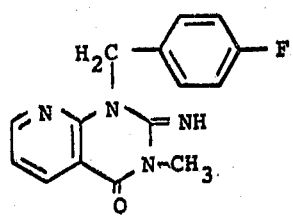

To a suspension of 0.4 g. of sodium hydride in 60 ml. of dimethylacetamide is added 2.5 g. of 1-(4'-fluorobenzyl)-2-amino-pyrido[2,3-d]pyrimidin-4(1H)-one while maintaining the system under nitrogen. After stirring for one hour at room temperature, the mixture is treated by addition of 1.0 ml. of methyliodide. The resulting mixture is stirred at 20°C. for 15 hours. A small amount of water (ca 1.0 ml.) is then added and the mixture evaporated in vacuo. The residue is treated with ice/water and the resulting precipitate is recovered by filtering, washed with water and dried. The dried precipitate is then dissolved in methylene chloride, treated with charcoal and filtered through neutral alumina. The filtrate is concentrated in vacuo and ether added to obtain on crystallization 1-(4'-fluorobenzyl)-2,3-dihydro-2-imino-3-methyl-pyrido[2,3-d]pyrimidin-4(1H)-one

EXAMPLE 4

Alternate Process for 1-(4'-fluorobenzyl)-2-methylamino-pyrido[2,3-d]pyrimidin-4(1H)-one.

STEP A: Preparation of S,3-dimethyl-1-[2-(4'-fluorobenzyl) amino]nicotinoyl thiourea

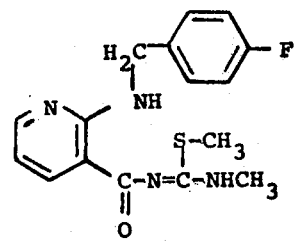

A mixture of 10 g. of 4-(4'-fluorobenzyl)-3,4-dihydro-1,3-dioxo-1H-pyrido[2,3-d][1,3]oxazine, 9.5 g. of S,N-dimethyl-thiopseudourea (hydrogen iodide), 6 g. of anhydrous potassium carbonate and 200 ml. of toluene is refluxed with stirring for 3½ hours. The resulting mixture is evaporated to dryness, dissolved in methylene chloride, filtered and extracted twice with ice cold 0.5 N hydrochloric acid. The organic phase is washed with water, treated with charcoal, dried, filtered through Celite, evaporated to dryness and chromatographed over silica gel using methylene chloride as the eluant. The head fractions contain a small amount of starting material. The further elutions are combined, evaporated and the residue combined with ether followed by cooling to obtain with scratching a precipitate which is recovered by filtering, washed with ice cold ether and dried under high vacuum to obtain S,3-dimethyl-1-[2-(4'-fluorobenzyl)amino]nicotinoyl thiourea, m.p. 84°–85°C.

STEP B: Preparation of 1-(4'-fluorobenzyl)-2-methylamino-pyrido[2,3-d]pyrimidin-4(1H)-one.

A mixture of 1.7 g. of S,3-dimethyl-1-[2-(4'-fluorobenzyl)amino]nicotinoyl thiourea, 0.5 g. of sodium hydroxide and 40 ml. of diglyme is refluxed for 3 hours and the resulting reaction mixture worked up in a manner similar to Example 1 to obtain 1-(4'-fluorobenzyl)-2-methylamino-pyrido[2,3-d]pyrimidin4(1H)-one, m.p. 242°–247°C.

EXAMPLE 5

1-(4'-fluorobenzyl)-2-allylamino-pyrido[2,3-d]pyrimidin-4(1H)-one.

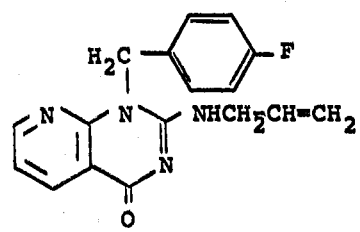

A mixture of 27 g. of 4-(4'-fluorobenzyl)-3,4-dihydro-1,3-dioxo-1H-pyrido[2,3-d][1,3]oxazine, 27.5 g. of S-methyl-N-allylthiopseudourea (hydrogen iodide), 12 g. of anhydrous sodium carbonate and 250 ml. of acetonitrile is refluxed with stirring for one hour. The resulting mixture is evaporated to dryness, the residue dissolved in methylene chloride filtered through celite and the filtrate evaporated in vacuo to obtain an oil of S-methyl-3-allyl-1-[2-(4'-fluorobenzyl) amino]nicotinoyl thiourea. This oil is dissolved in 150 ml. of diglyme and refluxed for 1.5 hours. The resulting reaction mixture is cooled and the resulting crystalline material is recovered by filtering, washed with diglyme and then twice with ether, dried in a high vacuum, dissolved in methylene chloride/methanol, filtered, concentrated on a steam bath and ether added to obtain 1-(4'-fluorobenzyl)-2-allylamino-pyrido 2,3-d pyrimidin-4(1H)-one, m.p. 190–194°C. 190°–

What is claimed is:

1. A compound of the formula

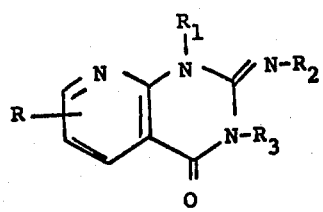

wherein $R_1$ is alkyl of 1 to 6 carbon atoms, alkenyl of 3 to 8 carbon atoms or phenalkyl of the formula:

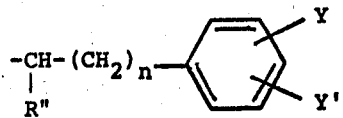

n is 0 or 1,
R'' is hydrogen or methyl provided that R'' is hydrogen when n is 1,
$R_2$ is hydrogen, alkyl of 1 to 6 carbon atoms or alkenyl of 3 to 6 carbon atoms,
$R_3$ is hydrogen, alkyl of 1 to 6 carbon atoms or alkenyl of 3 to 6 carbon atoms,
R is hydrogen or alkyl of 1 to 3 carbon atoms, and
Y and Y' are independently hydrogen, fluoro, chloro, alkyl of 1 to 3 carbon atoms or alkoxy of 1 to 3 carbon atoms or one is hydrogen and the other bromo or trifluoromethyl, or a pharmaceutically acceptable acid addition salt of the compounds in which each of $R_2$ and $R_3$ is hydrogen.

2. A compound of claim 1 in which $R_3$ is hydrogen.
3. A compound of claim 1 in which each of $R_2$ and $R_3$ is hydrogen.
4. A compound of claim 1 in which each of $R_2$ and $R_3$ is alkyl.
5. A compound of claim 2 in which $R_2$ is alkyl.
6. A compound of claim 5 in which $R_2$ is alkyl of 1 to 3 carbon atoms.
7. A compound of claim 1 in which $R_1$ is

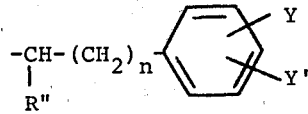

8. A compound of claim 7 in which R'' is hydrogen, n is 0, Y is hydrogen, fluoro, chloro or bromo and Y' is hydrogen, fluoro or chloro, with the proviso that Y' is hydrogen when Y is bromo.
9. A compound of claim 8 in which Y is 4-fluorobenzyl, 4-chlorobenzyl or 4-bromobenzyl and Y' is hydrogen.
10. A compound of claim 8 in which $R_2$ is hydrogen or alkyl and $R_3$ is hydrogen.
11. A compound of claim 10 in which R is hydrogen.
12. The compound of claim 11 which is 1-(4'-fluorobenzyl-2-methylimino-pyrido[2,3-d]pyrimidin-4(1H)-one.
13. The compound of claim 6 which is 1-(4'-fluorobenzyl)-2-ethylamino-pyrido[2,3-d]pyrimidin-4(1H)-one.
14. A compound of claim 1 in which $R_1$ is alkyl.
15. A compound of claim 1 in which $R_2$ and $R_3$ are hydrogen or alkyl.

* * * * *